United States Patent
Kleemiss et al.

(10) Patent No.: US 6,399,809 B1
(45) Date of Patent: Jun. 4, 2002

(54) PROCESS FOR THE PREPARATION OF AMINO ACID DERIVATIVES

(75) Inventors: Wolfgang Kleemiss, Haltern; Marcel Feld, Cologne, both of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/557,413

(22) Filed: Apr. 21, 2000

(30) Foreign Application Priority Data

Apr. 21, 1999 (DE) .......................................... 199 17 961

(51) Int. Cl.[7] ..................... C07C 205/00; C07C 229/00; C07C 261/00

(52) U.S. Cl. ............................. 560/24; 560/27; 560/38; 560/155; 560/157; 562/443; 562/555

(58) Field of Search ................................ 562/443, 555; 560/24, 27, 38, 155, 157

(56) References Cited

U.S. PATENT DOCUMENTS 4,486,603 A * 12/1984 Zengel et al.
5,079,167 A    1/1992 Sambale et al.
5,831,119 A * 11/1998 Bauer et al.

FOREIGN PATENT DOCUMENTS

| DE | 197 24 086 | 12/1997 |
| EP | 0 676 390 | 10/1995 |
| EP | 0 770 613 | 5/1997 |
| GB | 1130866 | * 10/1968 |

OTHER PUBLICATIONS

Cativiela et al. (1994). Approaches to the assymetric synthesis of a–methylphenylalanine. Tetrahedron: Assymetry 5(2): 261–268.*

Andreas S. Bommarius et al., "Biocatalysios To Amino Acid–Based Chiral Pharmaceuticals–Examples and Prespectives", Journal of Molecular Catalysis B: Enzymatic, vol. 5, pp. 1–11 (1998).

M. Crisma et al., "Peptides From Chiral $C^{\alpha\alpha}$–Disubstituted Glycines on the Helical Screw Sense of Isovaline Peptides", Recl. Trav. Chim. Pays–Bas vol. 114, pp. 325–331 (1995).

M. Crisma et al., "Peptides From Chiral $C^{\alpha\alpha}$–Disubstituted Glycines on the Helical Screw Sense of Isovaline Peptides", Recl. Trav. Chim. Pays–Bas vol. 114, pp. 325–311 (1995).

Sudhanand Prasad eT AL., "Contrasting Solution Conformation of Peptides Containig α, α–Dialkylated Residues With Linear and Cyclic Side Chains", Biopolymers, vol. 35, pp. 11–20 (1995).

Paul M. Hardy et al., "Peptides Containing Dipropylgycine", Int. J. Peptide Res. vol. 21, pp. 392–405, 1983.

W. Oldfield et al., "The Chemistry And Pharmacology of a Series of Cycloalkanespiro–5'–Hydantoins", J. Mod. Chem., vol. 8, pp. 239–249.Mar. 1965.

Von P.G. Waser et al., "Die Entwicklung Neuer Antiepileptika", Arzneim.–Forsch./Drug Res. vol. 27 (II), pp. 1942–1953, 1977. English Abstract.

R. K. Satsangi et al., 1–(4–Substituted–Thiazol–2–yl)Hydantoins as Anti–Inflammatory and CNS–Active Agents, Pharmazic, vol. 38, pp. 341–342, 1983.

Sergio Cortes et al., "Effect Of Structural Modification Of The Hydantoin Ring On Anticonvulsant Activity", J. Med. Chem., vol. 28, pp. 601–606, 1985.

Geoffrey W. Pang et al., "Potential Central Nervous System Antitumor Agents. Hydantoin Derivatives", Journal of Medicinal Chemistry, vol. 18, No. 8, 1975.

H. Fischer et al., "Investigation Of The Antitumor Activity Of New Epoxide Derivatives", Arzneim–Forsch./Drug Res., vol. 34 (I), pp. 663–668, 1984.

Yao–Tseng Huang et al., "AMIno Acids and Their Derivatives. III. Synthesis Of Aminodipropylacetic Acid", J. Chinese Chem. SOc., vol. 8, pp. 81–91, 1941, Chemical Abstracts, vol. 37, Columns 1387–1388.

Everett S. Wallis et al., "The Hofmann Reaction", Organic Reactions, Vol. III, Chapter 7, pp. 264–275, 1946.

(List continued on next page.)

*Primary Examiner*—Gary Geist
*Assistant Examiner*—Mahreen Chaudhry
(74) *Attorney, Agent, or Firm*—Oblon, Spivak, McClelland, Maier & Neustadt, P.C.

(57) ABSTRACT

Process for the preparation of amino acid derivatives of the general formula I

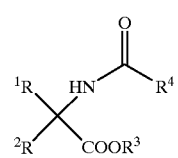

I where $R^1$–$R^4$ are as defined herein, from the corresponding malonic acid monoester amides of the general formula II

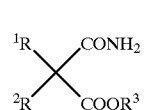

II by Hofmann degradation using a hypohalite in an aqueously basic medium, which comprises carrying out the reaction in the presence of an alcohol or amine and using the hypohalite in amounts of from 1.0 to 1.5 equivalents and the base in amounts of from 0.8 to 4.0 equivalents per mole of starting material II.

16 Claims, No Drawings

OTHER PUBLICATIONS

Andreas S. Bommarius et al., "L–Methionine Related L–Amino Acids by Acylase Cleavage Of Thier Corresponding N–Acetyl–DL–Derivatives", Tetrahedron: Asymmetry, vol. 8, No. 19, pp. 3197–3200, 1997.

Xicai Huang et al., "A Mild And Efficient Modified Hofmann Rearrangement", J. Org. Chem., vol. 62, pp. 7495–7496, 1997.

E. Wuensch, "30. Methodische Voraussetzungen, 31. Blockierung Und Schutz Der A–Amino–Funktion", pp. 47–51, 117–121, 1974. NO English Translation.

Carlos Cativiela et al., Chiral 2–Cyano Ester SAS Synthetic Intermediates in the Synthesis Of R and S α–Methylvaline, Tetrahedron, vol. 51, No. 20, pp. 5921–5928, 1995.

E. Lewke et al., "Enzymatic Cleavage Of Amino Acid Carbamates", Ann. N.Y. Acad. Sci., pp. 343–345, 1988.

Bruce A. Dressman et al, Solid Phase Synthesis Of Hydantoins Using A Carbamate Linker And A Novel Cyclization / Cleavage Step, Tetrahedron Letters, vol. 37, No. 7, pp. 937–940, 1996.

Liang Li Et Al, VI. Synthesis Of Alpha–Amino–Ethylpropylacetic Acid, Chemical Abstracts, vol. 38, No. 2, XP002147330, Jan. 20, 1944.

W. Treibts et al., Synthesen MIT Dicarbonsäuren, XIX. Mitteil.: Darstellung Von Omega–Aminocarbonsäuren Durch Halbesitigen Hoffmanschen Abbau von Dicarbonsäuren, XP 002147329, 1956.

* cited by examiner

PROCESS FOR THE PREPARATION OF AMINO ACID DERIVATIVES

BACKGROUND OF THE INVENTION

1. Field of the Invention

The present invention relates to a process for the preparation of amino acid derivatives of the general formula I

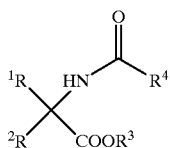

I where $R^1$ is $C_{1-6}$-alkyl or $C_{3-6}$-cycloalkyl and $R^2$ is $C_{1-6}$-alkyl, phenyl, heteroaryl-, $(CH_2)_{1-3}$-phenyl or $-(CH_2)_{1-4}-$COOR, or $R^1$ and $R^2$ together are $-(CH_2)_{2-6}$, $-(CH_2)_2-$O$-(CH_2)_2-$ or

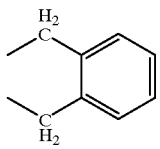

or $R^1$ is hydrogen and $R^2$ is a tertiary hydrocarbon radical having from 4 to 10 carbon atoms, $R^3$ is hydrogen or an alkyl radical having 1–4, in particular 1 or 2, carbon atoms and $R^4$ is OR, where R in $R^2$ and $R^4$ is an aliphatic, aromatic or araliphatic radical having from 1 to 8 carbon atoms, or NR'R", where R' is hydrogen or an aliphatic, aromatic or araliphatic radical having from 1 to 8 carbon atoms and R" is hydrogen or an aliphatic, aromatic or araliphatic radical having from 1 to 8 carbon atoms which may or may not be different from R', from the corresponding malonic acid monoester amides of the general formula II by Hofmann degradation using a hypohalite in an aqueously basic medium in the presence of an alcohol or amine

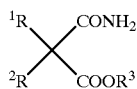

II where $R^1$, $R^2$ and $R^3$ are as defined above.

If $R^1$ is different to $R^2$, the compounds of the general formula II as well as the compounds of the general formula I are chiral. Thus, the racemates of the compounds of the general formula II also give the racemates of the amino acid derivatives of the general formula I. On the other hand, the corresponding enantiomerically pure compounds of the general formula II, where $R^1$ is not equal to $R^2$, also give the corresponding enantiomerically pure compounds of the general formula I.

2. Background of the Invention

Amino acids and derivatives thereof are of great importance for the synthesis of pharmacologically active compounds (A. S. Bommarius, M. Schwarm and K. Drauz, J. Mol. Catalysis B; Enzymatic 5 (1998) 1–11). In addition to the naturally occurring amino acids, the importance of unnatural amino acids and derivatives thereof is also increasing. For example, the synthesis of highly effective pharmaceutical products requires derivatives of specific unnatural amino acids. The development of suitable synthesis processes for the preparation of specific amino acids is thus of great interest.

Of the unnatural amino acids, the 2,2-dialkylaminoacetic acids, as unnatural amino acids, are of great importance for the synthesis of specific peptides. The additional alkyl group in the 2-position compared with the natural amino acids leads to conformative rigidity of the corresponding peptide bond and as a result influences in a manner which is relevant the tertiary structure of the overall peptide (D. Obrecht, M. Altorfer, U. Bohdal, J. Daly, W. Huber, A. Labhardt, C. Lehmann, K. Muller, R. Ruffieux, P. Schonholzer, C. Spiegler, C. Zumbrunn, Biopolymers 42(5), 575–626 (1997); M. Crisma, G. Valle, M. Pantano, F. Formaggio, G. M. Bonora, C. Toniolo, J. Kamphius, Recl. Trav. Chim. Pays-Bas 114(7), 325–31 (1995); S. Prasad, B. R. Rao, P. Balaram, Biopolymers 35(1), 11–20, (1995)).

2,2-Dialkylaminoacetic acids have also been used as lipophilic amino acids for the construction of peptides, which are important as potential active ingredient candidates (P. M. Hardy, l. N. Lingham, Int. J. Peptide Protein Res. 21, 392–405 (1983)).

Moreover, European Patent Application EP-A 770 613 describes the synthesis of 5,5-disubstituted imidazolidin-2,4-diones, which are used as immunodilators. Their synthesis starts from the corresponding 2,2-dialkyl amino acid esters.

Substituted hydantoin compounds, which can be prepared simply from the compounds of the general formula I where $R^4$=OR, where R is an aliphatic, aromatic or araliphatic radical having from 1 to 8 carbon atoms (B. A. Dressmann, L. A. Spangle, W. Kaldor, Tetrahedron Lett. 937–940 (1996)) are generally of great importance as pharmaceutical products or precursors. In the pharmaceutical field, anticonvulsive, antiinflammatory (J. Med. Chem. 8,239 (1965); Arzneim. Forsch./Drug Res. 27(11), 1942 (1977); Pharmazie 38,341 (1983), J. Med. Chem. 28,601 (1985)) and antitumor effects (J. Med. Chem. 18,846 (1975); Arzneim. Forsch./Drug Res. 34(1), 663 (1984)) in particular are known.

The synthesis of ethyl 2,2-di-n-propylaminoacetate has been described starting from ethyl cyanoacetate (J. Chinese Chem. Soc. 8, 81–91 (1941)), shown in Equation 1 below:

Equation 1

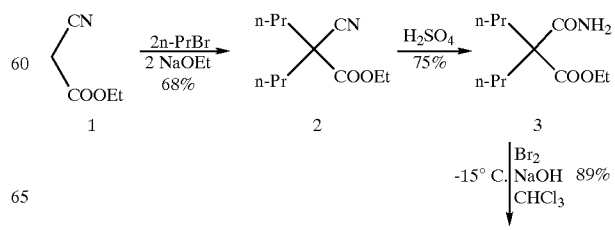

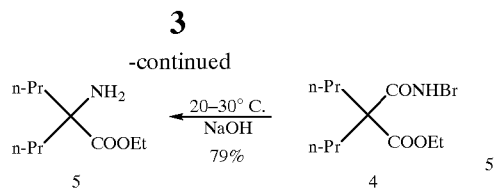

For this purpose, the ethyl cyanoacetate was first converted into the enolate using sodium ethoxide, and then reacted with 2 equivalents of propyl bromide. The ethyl 2,2-di-n-propylcyanoacetate 2, obtained in a yield of 68%, was then converted into the 2,2-di-n-propylmalonic acid monoamide ethyl ester 3 in a yield of 75% using sulfuric acid. Reaction with a mixture of sodium hydroxide solution and bromine in chloroform then gave the 2,2-di-n-propyl-n-bromomalonic acid monoamide ethyl ester 4 in a yield of 89%. The latter was then converted into the target compound 5 using an excess of sodium hydroxide solution by Hofmann degradation in a yield of 79%. The overall yield starting from ethyl cyanoacetate was thus 36%.

The synthesis of this compound, which can also be called di-n-propylglycine ethyl ester, was later optimized (P. M. Hardy, l. N. Lingham, Int. J. Peptide Protein Res. 21, 392–405 (1983)). The synthesis of ethyl 2,2-di-n-propylcyanoacetate 2 gave a yield of 81%, while the subsequent reaction to give the 2,2-di-n-propylmalonic acid monoamide ethyl ester 3 gave a yield of 82%. Following further reaction with bromine and NaOH in CHCl$_3$ at low temperature, the N-bromoamide 4 was not isolated, but, following treatment with a 4-fold excess of sodium hydroxide solution, the corresponding isocyanate 6 in a distillative yield of 81% was obtained. The latter was then refluxed with an excess of 3M HCl. Subsequent alkalinization with sodium hydroxide solution gave the amino ester 5 in a yield of 87%. The overall yield of this synthesis was about 47% starting from cyanoacetic ester 1.

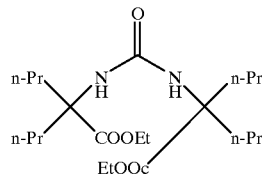

Hardy et al. emphasize that the isolation of the isocyanate and the subsequent acidic hydrolysis to give the amino ester 5 is of great advantage since in this method the formation of a urea derivative 7, which is very problematic during work-up, is avoided. This is because, under alkaline conditions, some of the reaction product 5 reacts with the isocyanate 6 to give the problematic urea derivative 7, which, furthermore, considerably reduces the yield.

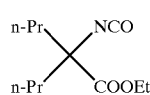

Despite the higher yield which Hardy et al. achieved with their synthesis strategy, the process according to equation 1 has a number of problems. For example, the carrying out of the Hofmann degradation in chloroform using a mixture of bromine and sodium hydroxide solution is surely only suitable as a laboratory method. Also, a reaction temperature of −15° C. can only be attained in industry at great expense. Another disadvantage of the process is the need to isolate the isocyanate in order to prevent the formation of the urea derivative 7. This is, firstly, an additional step and, secondly, requires subsequent acidic hydrolysis to give the amino acid ester 5. In this connection, salt is again produced in stoichiometric amounts since it is necessary to alkalinize the reaction mixture prior to extraction of the product.

Against the backdrop of the large synthesis expenditure for the preparation of 5, the overall yield of 47% in total starting from cyanoacetic ester 1 is thus unsatisfactory. The yield of the Hofmann degradation reaction of 3 to produce 5 is about 70%.

Another method for the preparation of the amino ester 5 starts from a racemic norvaline, an unnatural amino acid (EP 770613), shown in Equation 2 below:

Equation 2

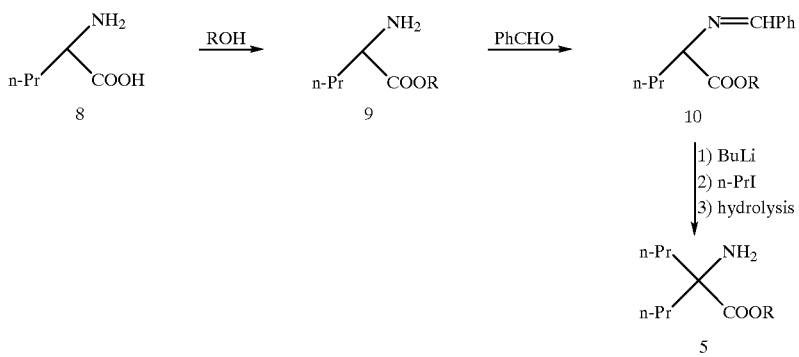

Here, the amino acid is first converted into the ester. Then, by reaction with benzaldehyde, an imine is synthesized, which is converted to the di-n-propylglycine ester by deprotonation using n-butyllithium and alkylation using propyl iodide with subsequent hydrolysis. The overall yield for all of the stages is only 53%.

Apart from the fact that the starting compound for the synthesis, norvaline, is significantly more expensive than cyanoacetic ester, the individual steps, apart from the esterification stage, can only be carried out with difficulty in industry or are associated with very high costs. In the second stage, benzaldehyde is used in stoichiometric amounts and must be cleaved off again following alkylation.

The alkylation is, moreover, carried out using expensive propyliodide. In addition, the alkylation requires n-butyllithium as base. This base is, however, firstly expensive and, secondly, can only be handled in industry under strict safety precautions.

Another problem, which applies to both of the syntheses described in Equations 1 and 2, is the generation of large amounts of waste salt. If the syntheses are carried out on a large scale, disposal of the waste salt leads to high costs. In the process in accordance with Equation 2, moreover, the salt which forms in the synthesis of the starting material 8 must be taken into account.

Accordingly, there remains a need for processes which overcome these disadvantages.

SUMMARY OF THE INVENTION

It is an object of the present invention to provide a process for the preparation of amino acid derivatives of the general formula I from which the corresponding amino acid derivatives containing a free amino group or the amino acids themselves can be prepared in a simple manner.

It is another object of the invention to provide a process for the preparation of amino acid derivatives of the general formula I starting from inexpensive starting materials that gives good yields and space-time yields, does not require substances which are demanding from the point of view of safety and which permits extremely simple work-up of the product without complex removal of reaction salts.

The objects of the invention, and others, may be accomplished with a process for the preparation of an amino acid derivative represented by formula I:

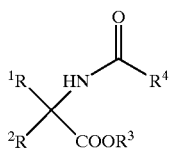

where
$R^1$ is $C_{1-6}$-alkyl or $C_{3-6}$-cycloalkyl, and
$R^2$ is $C_{1-6}$-alkyl, phenyl, heteroaryl-, $(CH_2)_{1-3}$-phenyl or —$(CH_2)_{1-4}$—COOR, or
$R^1$ and $R^2$ together are—$(CH_2)_{2-6}$, —$(CH_2)_2$—O —$(CH_2)_2$— or

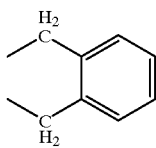

or $R_1$ is hydrogen and $R^2$ is tertiary hydrocarbon radical having from 4 to 10 carbon atoms,
$R^3$ is hydrogen or an alkyl radical having 1–4 carbon atoms, and
$R^4$ is —OR or —NR'R",
wherein R in the definition of $R^2$ and $R^4$ is, independently, an aliphatic, aromatic or araliphatic radical having from 1 to 8 carbon atoms,
R' is hydrogen or an aliphatic, aromatic or araliphatic radical having from 1 to 8 carbon atoms,
R" is hydrogen or an aliphatic, aromatic or araliphatic radical having from 1 to 8 carbon atoms, comprising:

reacting a malonic acid monoester amide represented by formula II:

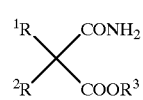

wherein $R^1$, $R^2$ and $R^3$ are as defined above, with a hypohalite in a basic aqueous medium and then with an alcohol represented by the formula R—OH or an amine represented by the formula HNR'R", wherein R, R' and R" are as defined above.

In the present invention, the objects maybe achieved, and amino acid derivatives of the general formula I are advantageously prepared, by reacting malonic acid monoester amides of the general formula II in a Hofmann degradation with, in particular, from 1.0 to 1.2 equivalents of a hypohalite solution and from 1.0 to 4.0 equivalents of an alkali metal hydroxide in the presence of an aliphatic, aromatic or araliphatic alcohol having from 1 to 8 carbon atoms or an aliphatic, aromatic or araliphatic primary or second amine having from 1 to 16 carbon atoms, or ammonia.

The objects of the present invention may also be accomplished with a process in which the amino acid derivatives represented by formula I are converted to the corresponding free amino or amino salt.

A more complete appreciation of the invention and many of the attendant advantages thereof will be readily obtained as the same becomes better understood by reference to the following detailed description.

DETAILED DESCRIPTION OF THE INVENTION

The Hofmann degradation (a.k.a. Hofmann rearrangement) of substituted malonic ester amides usually directly results in the free amino acids in the form of their salts (EP-A 0 676 390, DE 197 24 086). These salts are very readily soluble in water. The amino acids must then be separated off from the likewise water-soluble reaction salt in complex extraction methods or ion exchange methods.

If the reaction is carried out according to the invention, in addition to small amounts of the corresponding amino acids or their esters, the corresponding N-alkoxycarbonylamino acids or N-carbamoylamino acids or their esters form. These compounds can, after the alcohol or amine excess has been removed and optionally after acidification of the resulting reaction mixture, be isolated by extraction using an organic solvent.

The fact that the Hofmann degradation of amines with alkali metal hypohalite in the presence of alcohols leads to the corresponding carbamates is known per se (E. S. Wallis, J. F. Lane, Organic Reactions lil, [1946], 267–306). Use of this reaction method for substituted malonic acid monoamide esters of the general formula I is, however, novel. It is surprising that, depending on the substitution pattern on the malonate carbon atom, the Hofmann degradation of compounds of the general formula II in the presence of an alcohol or amine as well as small amounts of the corresponding amino acids or their esters leads either to the free N-alkoxycarbonylamino acid, or N-carbamoylamino acid or to the corresponding esters. The esters can be isolated after distillative removal of the alcohol or amine excess by extraction using an organic solvent, while the free acids can only be obtained after acidification of the reaction discharge freed from solvent by extraction with an organic solvent (e.g. methyl tert-butyl ether, diethyl ether, toluene, cyclohexane).

Complex separation of reaction product and reaction salts which are present together in the aqueous phase by ion exchange chromatography or special membrane methods is thus unnecessary.

The conventional processes for the preparation of amino acids (Strecker synthesis, all biotechnology methods and others) produce amino acid and reaction salt together in aqueous solution. Complex methods to separate the reaction product from the reaction salt are necessary in these methods.

Another advantage of the process of the present invention is that the use of a very much smaller excess of alkali than that used by Hardy et al. leads to good yields of the N-alkoxycarbonylamino acids or N-carbamoylamino acids or their corresponding esters.

Even the use of one equivalent of alkali metal hydroxide based on the malonic acid monoamide ester of the general formula II leads to good yields of compounds of the general formula I.

The direct formation of the N-alkoxycarbonylamino acids, or N-carbamoylamino acids or their corresponding esters is also very interesting in as much as synthesis methods are being sought in the pharmaceutical and agricultural field, which permit the simple preparation of derivatives of specific amino acids, which in turn are to be used for racemate resolution into the enantiomers. In this connection, these are, for example, the N-acylamino acids (A. S. Bommarius, K. Drauz, K. Gunther, G. Knaup and M. Schwarm, Tetrahedron: Asymmetry 3197–3200 (1997)) or the N-alkoxycarbonyl derivatives of the corresponding amino acids (DE 36 06 401; Ann. N. Y. Acad. Sci (Enzyme 9), 343–345 (1988)).

The Hofmann degradation requires a base and a hypohalite, i.e. a salt of a hypohalous acid. Of the hypohalite solutions, the readily accessible, inexpensive hypochlorites are preferably used. The preferred hypochlorites are alkali metal hypochlorites such as potassium hypochlorite and, in particular, sodium hypochlorite in the form of their aqueous solution, which is also referred to as bleaching liquor. Calcium hypochlorite can also be used but may give lower yields. The hypohalite is used in an amount of from 1.0 to 1.5, preferably from 1.0 to 1.2, equivalents, based on the starting material II.

Preferred bases are the alkali metal hydroxides, such as potassium hydroxide and, in particular, sodium hydroxide, again in the form of their aqueous solutions. Alkaline earth metal hydroxides are also suitable, but give lower yields. In general, a base with a cation which is also present in the hypohalite is used. The base is used in an amount of from 0.8 to 4.0, preferably from 0.8 to 1.5, equivalents per equivalent of the starting material II.

The reaction takes place in an aqueous basic medium in the presence of a 2- to 20-fold molar excess of the alcohol or amine. In general, the water makes up from 30 to 80, in particular from 40 to 80% by weight of the reaction mixture.

Alcohols which can be used are primary, secondary or tertiary alcohols having from 1 to 8 carbon atoms, such as, for example, methanol, ethanol, isopropanol, t-butanol, 2-ethylhexanol, benzyl alcohol, etc. In addition to ammonia, it is also possible to use primary or secondary amines having from 1 to 16 carbon atoms, such as, for example, diethylamine, di-n-propylamine, butylamine or benzylamine.

The process of the present invention may be carried out continuously or discontinuously. In a discontinuous procedure using alkali metal hydroxide such as, for example, sodium hydroxide, as base and a hypochlorite such as, for example, sodium hypochlorite as salt of a hypohalous acid in the presence of an alcohol or an amine, the reaction is first carried out at a temperature which is generally from 0 to 20° C., preferably from 5 to 10° C., with a reaction time of from 0.25 to 10 hours, preferably from 0.5 to 4 hours, and the resulting reaction mixture is heated to a temperature of from 40 to 100° C., preferably from 60 to 80° C. Depending on the temperature, the reaction is complete after from 2 minutes to 2 hours.

According to the inventive process, the starting material of the general formula II can also be reacted initially only with the aqueous hypochlorite solution at a temperature of from 0 to 20° C., preferably from 5 to 10° C., for from 0.5 to 4 hours, and, after addition of the alkali metal hydroxide, this cold reaction mixture is then introduced into a from 2- to 20-fold excess of an alcohol or an amine, optionally in aqueous solution, at a temperature of from 40 to 100° C., preferably from 60 to 80° C.

After the reaction mixture has been cooled, the product I, optionally after prior distillative or extractive removal of the alcohol or amine, is separated off as organic phase. The aqueous, lower phase can be extracted using an inert organic solvent in order to isolate further product. The combined organic phases can, following drying over, for example, a molecular sieve or water-binding salts (magnesium sulfate, sodium sulfate etc.), be freed from the organic solvent. This gives the crude product I, which can be purified by distillation and/or extraction with an inert organic solvent. This gives the product with high purity and in a yield of >80%. In order to obtain more crude product of the general formula I where $R^3$=H, the remaining aqueous phase can be acidified and again extracted with an inert organic solvent to completion.

The reaction procedure of the present process largely prevents the formation of undesired urea derivatives, which are analogous to the compound of the formula 7. Surprisingly, the undesired dimerisation reaction to give the corresponding urea derivatives under the conditions according to the invention is suppressed.

In this way it is thus possible to prepare the N-alkoxycarbonylamino acids, or N-carbamoylamino acids or their corresponding esters of the general formula I in high yield and with high selectivity.

Here, there is no need to isolate the unstable isocyanate analogous to formula 6 and, in a separate step, to carry out the hydrolysis to give the end product in concentrated hydrochloric acid.

Although the conversion of aromatic or aliphatic amides into the methylcarbamates by Hofmann-analogous reaction conditions has been described in principle (W. Keillor et al., J. Org. Chem. 62, 7495–7496 (1997)), the conditions are without exception only suitable for laboratory scale. Thus, the corresponding amide is reacted with two equivalents of N-bromosuccinimide in the presence of an amidine base and with methanol as solvent to give the corresponding methylcarbamate in yields of from 40 up to a maximum of 95%. Keillor et al. have not described the reaction of substituted malonic acid monoester amides of the general formula II with N-bromosuccinimide to give the corresponding methyl carbamates of the corresponding amino acetates of the general formula I.

N-bromosuccinimide is very much more expensive than alkali metal hypohalite, in particular sodium hypochlorite. In addition, under the reaction conditions given by Keillor et al., 2 equivalents of succinimide result, which have to be disposed of. In industrial production, the disposal costs for the succinimide would be unacceptable.

In the inventive process described herein, on the other hand, the alkali metal hypohalite, in particular sodium hypochlorite, gives the alkali metal halide, in particular sodium chloride, in the form of its aqueous solution. This can be disposed of without difficulty.

Carbamates of the general formula I can in turn be very easily converted into the corresponding amino acids (Houben Weyl 15/1, 117 (1974); C. Cativiela, M. D. Diaz-de-Villegas, J. A. Galvez, Y. Lapena, Tetrahedron 51, 5921–28 (1995)). N-carbamoylaminoacetic acid derivatives of the general formula I in which $R_4$ is NR'R", and R' is an aliphatic, aromatic or araliphatic radical having from 1 to 8 carbon atoms, and R" is hydrogen or an aliphatic, aromatic or araliphatic radical having from 1 to 8 carbon atoms which may or may not be different to R', are, however, also highly interesting starting compounds for the synthesis of substituted hydantoins, as are described, for example, in EPA-0 770 613, incorporated herein by reference.

N-alkoxycarbonylamino acids, or N-carbamoylamino acids or their corresponding esters of the general formula I are, of course, also accessible starting from the corresponding amino acids. However, for this purpose, the amino acid in question must be easily accessible. In addition, the amino acid or its ester must then be reacted with phosgene or a phosgene derivative and then with alcohol or amine (Houben Weyl 15/1, 46 (1974)). Phosgene is highly toxic and can only be handled under strict safety precautions. Against this background, too, the process according to the invention has great advantages since N-alkoxycarbonylamino acids, or N-carbamoylamino acids or their corresponding esters of the general formula I can be prepared without using highly toxic phosgene or phosgene derivatives.

EXAMPLES

Having generally described this invention, a further understanding can be obtained by reference to certain specific examples which are provided herein for purposes of illustration only and are not intended to be limiting unless otherwise specified.

Example 1

60.0 g (0.28 mol) of 2,2-di-n-propylmalonic acid monoethyl ester amide are dissolved in 300 g of methanol in a stirred vessel. 58.0 g (0.29 mol) of 20% strength sodium hydroxide solution and 263.4 g (0.33 mol) of 9.3% strength sodium hypochlorite solution are added to the solution, which has been cooled to 5° C., at a rate such that the temperature of the reaction mixture does not exceed 10° C. The mixture is then stirred for 1 h at about 5° C., and then the resulting suspension (during the chlorination an inorganic salt precipitates out) is continuously metered over a frit in order to separate off the salt. The clear filtrate is metered continuously through a tubular reactor heated to 68° C. The volume of the tubular reactor and the metered amount per time is chosen such that a residence time of the filtrate in the tubular reactor of from 2 to 3 minutes is ensured. After the filtrate has been metered through the reactor, 200 ml of methanol are pumped through. The reaction product is freed from methanol at a pressure of 40 mbar and a temperature of 40° C. The residue is extracted with methyl t-butyl ether (MTBE) until exhaustion. The organic phases are combined and dried. The solvent is then distilled off to leave 57.3 g of an oil, >97% of which, according to $^{13}$C-NMR spectrum, consists of ethyl N-methoxycarbonyl-2,2-di-n-propylaminoacetate (81% yield). The subsidiary constituent is ethyl 2,2-di-n-propylaminoacetate (3% yield).

The amino acid di-n-propylglycine can be obtained in the form of its hydrochloride by combining the ethyl N-methoxycarbonyl-2,2-di-n-propylaminoacetate and the ethyl 2,2-di-n-propylaminoacetate and refluxing the mixture with concentrated hydrochloric acid for 12 hours. After cooling, the solution is extracted with MTBE, and the aqueous solution is evaporated to dryness. The residue is taken up again in water, and the solution is evaporated under reduced pressure in order to remove excess hydrochloric acid to leave 43.8 g (80%) of di-n-propylglycine hydrochloride. This can be used to obtain the free amino acid in accordance with known methods.

Example 2

60.0 g (0.32 mol) of 2,2-diethyl malonic acid monoethyl ester amide are dissolved in 300 g of methanol in a stirred vessel. 65.0 g (0.33 mol) of 20% strength sodium hydroxide solution and 280.2 g (0.35 mol) of 9.3% strength sodium hypochlorite solution are added to the solution, which has been cooled to 5° C., at a rate such that the temperature of the reaction mixture does not exceed 10° C. The mixture is then stirred for 1 h at about 5° C., and then the resulting suspension (during the chlorination an inorganic salt precipitates out) is continuously metered over a frit in order to separate off the salt. The clear filtrate is metered continuously through a tubular reactor heated to 68° C. The volume of the tubular reactor and the metered amount per time is chosen such that a residence time of the filtrate in the tubular reactor of from 2 to 3 minutes is ensured. After the filtrate has been metered through the reactor, 200 ml of methanol are pumped through. The reaction product is freed from methanol at a pressure of 40 mbar and a temperature of 40° C. The residue is extracted with MTBE until exhaustion. The organic phases are combined and dried. The solvent is then distilled off to leave 49.1 g of an oil, >85% of which, according to $^{13}$C-NMR spectrum, consists of ethyl N-methoxycarbonyl-2,2-diethylaminoacetate (60% yield). The subsidiary constituent is ethyl 2,2-diethylaminoacetate (12% yield).

The aqueous, alkaline phase which remains after extraction is acidified with dilute hydrochloric acid and then extracted again to exhaustion with MTBE. This gives 5.8 g of an oil, 80% of which, according to $^{13}$C-NMR spectroscopy, consists of N-methoxycarbonyl-2,2-diethylamincacetic acid (8% yield) and 20% of which consists of 2,2-diethylaminoacetic acid (3% yield).

As described in Example 1, the amino acid derivatives ethyl N-methoxycarbonyl-2,2-diethylaminoacetate, ethyl 2,2-diethylamino acetate and N-methoxycarbonyl-2,2-diethylamino acetic acid can be reacted with concentrated hydrochloric acid to give the hydrochloride of diethylglycine.

Example 3

60.0 g (0.32 mol) of cyclopentane-1-carboxylic acid ethyl ester 1-carboxamide are dissolved in 300 g of methanol in a stirred vessel. 64.0 g (0.32 mol) of 20% strength sodium hydroxide solution and 264.5 g (0.33 mol) of 9.3% strength sodium hypochlorite solution are added to the solution, which has been cooled to 5° C., at a rate such that the temperature of the reaction >5 mixture does not exceed 10° C. The mixture is then stirred for 1 h at about 5° C., and then the resulting suspension (during the chlorination an inorganic salt precipitates out) is continuously metered over a frit in order to separate off the salt. The clear filtrate is metered continuously through a tubular reactor heated to 68° C. The volume of the tubular reactor and the metered amount per time is chosen such that a residence time of the filtrate in the tubular reactor of from 2 to 3 minutes is ensured. After the filtrate has been metered through the reactor, 200 ml of methanol are pumped through. The reaction product is freed from methanol at a pressure of 40 mbar and a temperature of 40° C. The residue is extracted with MTBE until exhaustion. The organic phases are combined and dried. The solvent is then distilled off to leave 7.1 g of an oil, >97% of which, according to $^{13}$C-NMR spectrum, consists of ethyl N-methoxycarbonyl-1-aminocyclopentanecarboxylate (yield: 10% ).

The aqueous, alkaline phase which remains after extraction is acidified with dilute hydrochloric acid and then extracted again to exhaustion with MTBE. This gives 43.0 g of an oil, 97% of which, according to $^{13}$C-NMR spectroscopy, consists of N-methoxycarbonyl-1-aminocyclopentanecarboxylic acid (70% yield).

As described in Example 1, the amino acid derivatives ethyl N-methoxycarbonyl-1-aminocyclopentanecarboxylate and N-methoxycarbonyl-1-aminocyclopentane-carboxylic acid can be reacted with concentrated hydrochloric acid to give the hydrochloride of 1-minocyclopentanecarboxylic acid.

Example 4

20.0 g (0.11 mol) of t-butylmalonic acid monoethyl ester amide are dissolved in 112 g of methanol in a stirred vessel. 22.0 g (0.10 mol) of 20% strength sodium hydroxide solution and 86.0 g (0.10 mol) of 9.3% strength sodium hypochlorite solution are added to the solution, which has been cooled to 5° C., at a rate such that the temperature of the reaction mixture does not exceed 10° C. The mixture is then stirred for 3 h at about 5° C., and then the resulting suspension (during the chlorination an inorganic salt precipitates out) is continuously metered over a frit in order to separate off the salt. The clear filtrate is metered continuously through a tubular reactor heated to 66° C. The volume of the tubular reactor and the metered amount per time is chosen such that a residence time of the filtrate in the tubular reactor of from 2 to 3 minutes is ensured. After the filtrate has been metered through the reactor, 200 ml of methanol are pumped through. The reaction product is freed from methanol at a pressure of 40 mbar and a temperature of 40° C. The residue is extracted with MTBE until exhaustion. The organic phases are combined and dried. The solvent is then distilled off to leave 9.7 g of an oil, >98% of which, according to $^{13}$C-NMR spectrum, consists of ethyl N-methoxycarbonyl-t-butylaminoacetate (40% yield).

The aqueous, alkaline phase which remains after extraction is acidified with dilute hydrochloric acid and then extracted again to exhaustion with MTBE. This gives 10.4 g of a solid (m.p.: 98–100° C.), >98% of which, according to $^{13}$C-NMR spectroscopy, consists of N-methoxycarbonyl-t-butylamiminiacetic acid (49% yield).

As described in Example 1, the amino acid derivatives ethyl N-methoxycarbonyl-t-butylaminoacetate and N-methoxycarbonyl-t-butylaminoacetic acid can be reacted with concentrated hydrochloric acid to give the hydrochloride of tert-leucine.

Example 5

20 g (0.093 mol) of 2,2-dipropylmalonic acid monoethyl ester amide are dissolved in 50 g of methanol in a stirred vessel. 18.6 g (0.092 mol) of 20% strength sodium hydroxide solution and 87.8 g (0.11 mol) of 9.3% strength sodium hypochlorite solution are added to the solution, which has been cooled to 5° C., at a rate such that the temperature of the reaction mixture does not exceed 10° C. The reaction is then stirred for 1 h at about 5° C., and then the resulting reaction mixture is continuously metered into a mixture of 24.6 g (0.23 mol) of benzylamine and 9.0 g of methanol heated to 60° C. with stirring. Following the metered addition, the prechlorination vessel is flushed with 15.0 g of methanol, and the resulting solution is likewise added to the benzylamine/methanol mixture. The mixture is left to react for 0.5 h at 65° C. The reaction product is freed from methanol at a temperature of 40° C. The residue is extracted to exhaustion with MTBE. The organic phases are combined and dried. The solvent is then distilled off to leave 40.3 g of an oil. This oil is taken up in MTBE, and the resulting solution is extracted with dilute hydrochloric acid in order to remove the excess of benzylamine. The MTBE solution is washed with water and then dried. Distillative removal of the MTBE leaves 23.7 g of an oil, from which a solid crystallizes out. The mixture is taken up in cyclohexane, the solid is separated off by filtration and washed with a small amount of cyclohexane to give 22.8 g of solid having a melting point of 80–83° C. The solid is N-2-(2-propylpentanoic acid)-N'-benzylurea. The yield is 84%.

Obviously, numerous modifications and variations of the present invention are possible in light of the above teachings. It is therefore to be understood that within the scope of the appended claims, the invention may be practiced otherwise than as specifically described herein.

This Application is based on German Patent Application Serial No. 199 17 961.1, filed on Apr. 21, 1999, and incorporated herein by reference in its entirety.

What is claimed is:
1. A process for the preparation of an amino acid derivative represented by formula I:

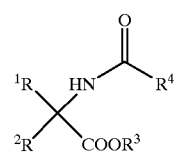

wherein
R$^1$ is C$_{1-6}$-alkyl or C$_{3-6}$-cycloalkyl, and
R$^2$ is C$_{1-6}$-alkyl, phenyl, heteroaryl-, (CH$_2$)$_{1-3}$-phenyl, or
R$^1$ and R$^2$ together are —(CH$_2$)$_{2-6}$, or

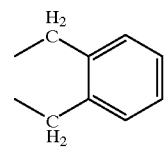

or R$^1$ is hydrogen and R$^2$ is a tertiary hydrocarbon radical having from 4 to 10 carbon atoms,
R$^3$ is hydrogen or an alkyl radical having 1–4 carbon atoms, and
R$^4$ is —OR or —NR'R",
wherein R in the definition of R$^4$ is, independently, an aliphatic, aromatic or araliphatic radical having from 1 to 8 carbon atoms, R' is hydrogen or an aliphatic, aromatic or araliphatic radical having from 1 to 8 carbon atoms, R" is hydrogen or an aliphatic, aromatic or araliphatic radical having from 1 to 8 carbon atoms, comprising: reacting a malonic acid monoester amide represented by formula II:

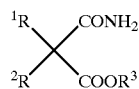

wherein $R^1$, $R^2$ and $R^3$ are as defined above, with a hypohalite in a basic aqueous medium, and then with an alcohol represented by the formula R—OH or an amine represented by the formula HNR'R", wherein R, R' and R" are as defined above, thereby forming an organic phase and an aqueous phase, and then recovering said amino acid derivative of formula I from said organic phase and said aqueous phase.

2. The process of claim 1, wherein the reaction occurs via the Hofmann degradation.

3. The process of claim 1, wherein $R^3$ is an alkyl radical having 1–2 carbon atoms.

4. The process as claimed in claim 1, wherein the hypohalite is used in amounts of from 1.0 to 1.5 equivalents and the base is used in amounts from 0.8 to 4.0 equivalents, per mole of the malonic acid monoester amide represented by formula II.

5. The process of claim 1, wherein the alcohol has from 1 to 8 carbon atoms or the amine has from 1 to 16 carbon atoms.

6. The process of claim 1, wherein the hypohalite is used in an amount of from 1.0 to 1.5 equivalents and the base is used in amounts of from 0.8 to 1.5 equivalents, per mole of the malonic acid monoester amide represented by formula II.

7. The process of claim 1, wherein the hypohalite used is an alkali metal hypochlorite, and the base is an alkali hydroxide.

8. The process of claim 7, wherein the alkali metal hypochlorite is sodium hypochlorite, and the alkali metal hydroxide is sodium hydroxide.

9. The process of claim 1, wherein the malonic acid monoester amide is firstly reacted in the precence of a hypochlorite solution at 0–20°C. for from 0.5 to 4 hours and then, after addition of the alkali metal hydroxide, is introduced at a temperature of from 40 to 100°C. into an alcohol or an amine.

10. The process of claim 1, wherein the malonic acid monoester amide is reacted in the presence of a hypochlorite solution and alkali metal hydroxide solution at 0–20° C. for from 0.5 to 4 hours and then, at a temperature of from 40 to 100° C., introduced into an alcohol or an amine.

11. The process of claim 1, wherein $R^4$ is —NR'R" and R' and R" are the same.

12. The process of claim 1, wherein $R^4$ is —NR'R" and R' and R" are different.

13. The process of claim 1, wherein at least one of R' and R" is an aliphatic, aromatic or araliphatic radical having from 1 to 8 carbon atoms.

14. The process of claim 1, wherein $R^4$ is —OR.

15. The process of claim 1, wherein $R^4$ is —NR'R".

16. The process of claim 1, wherein further comprising converting the amino acid derivative represented by formula I to the corresponding free amino or amine salt.

* * * * *